United States Patent [19]
Vacher et al.

[11] Patent Number: 6,001,366
[45] Date of Patent: Dec. 14, 1999

[54] **SLIMMING COSMETIC COMPOSITION CONTAINING A *CHRYSANTHELLUM INDICUM* EXTRACT**

[75] Inventors: Anne-Marie Vacher, Le Chesnay; Marie-Claire Fritsch, Paris, both of France

[73] Assignee: Lanatech Laboratoire Nature et Technique, France

[21] Appl. No.: 09/125,528

[22] PCT Filed: Dec. 18, 1997

[86] PCT No.: PCT/FR97/02344

§ 371 Date: Aug. 20, 1998

§ 102(e) Date: Aug. 20, 1998

[87] PCT Pub. No.: WO98/30200

PCT Pub. Date: Jul. 16, 1998

[30] Foreign Application Priority Data

Jan. 9, 1997 [FR] France ................... 97 00323

[51] Int. Cl.$^6$ .................. A61K 35/78; A61K 7/00
[52] U.S. Cl. ................ 424/195.1; 424/400; 424/401
[58] Field of Search ................... 424/400, 401, 424/195.1

[56] References Cited

U.S. PATENT DOCUMENTS 4,842,859  6/1989  Liu ........................ 424/195.1

FOREIGN PATENT DOCUMENTS

| 0317453 | 5/1989 | European Pat. Off. |
| 0493151 | 7/1992 | European Pat. Off. |
| 2233071 | 1/1975 | France. |
| 2456116 | 12/1980 | France. |
| 2618071 | 1/1989 | France. |

OTHER PUBLICATIONS

Z. Zhang, Dec. 27, 1995–XPOO2044018 and CN 1 113 691 Abstract Only in English.

T. Brasseur: Medicaments Renfermant des Flavonoides, Journal De Pharmacie De Belgigue, vol.44,No. 6, 1989, pp. 403–410, XPOO2044569, see p. 409 paragraph 2 —Abstract Only in English.

*Primary Examiner*—Shelley A. Dodson
*Attorney, Agent, or Firm*—William A. Drucker

[57] ABSTRACT

The invention concerns a slimming composition containing an chrysanthellum indicum extract with low concentration comprising 0.0001% to 0.1% of *Chrysanthellum indicum* dry extract equivalent. This composition is useful for the preventive and/or curative treatment of cellulitis.

38 Claims, No Drawings

SLIMMING COSMETIC COMPOSITION CONTAINING A *CHRYSANTHELLUM INDICUM* EXTRACT

The present invention relates to a cosmetic slimming composition which can be administered via the external topical route and which can be used in particular, but not exclusively, for the preventive and/or curative treatment of cellulite.

In general, it is known that in women, the fatty tissue located in the hypodermis represents 15 to 20% of the body weight. It is unevenly distributed on the hips, the buttocks and the abdomen in particular.

The hypodermis is hydrolipidic: 85% fatty substances and 15% water (⅔ of which is extracellular). This "fatty cushion" consists of lipid cells, the adipocytes. These large vacuolized cells almost entirely filled with triglycerides, the adipocytes, are regrouped in lobules delimited by connectivovascular partitions.

In women, these partitions are vertical and perpendicular to the skin's surface. In contrast, in men, they are arranged in an oblique manner. This difference explains why "orange-peel" skin is a typically female manifestation.

The connective part includes collagen fibres, reticulin fibres and reticuloendothelial cells. Vascularization is ensured by an artery and two veins for each lobule and by a great number of capillaries which run through the lobules and hold each adipocyte.

This proximity is fundamental for the transfer of lipids from the adipocyte into the systemic circulation, and vice versa.

In addition to this important vascularization, there is a rich lymphatic network and innervation which runs into the hypodermis before ending in the subjacent dermis.

The adipocytes, which are essential cells of fatty tissue, represent a major energy reserve.

The lipid reserves of adipose tissue are in a state of continual renewal, which is a sign of particularly active cell metabolism, the consequence of which is a rapid "turn-over" of lipids.

This metabolism includes three phases: lipogenesis (biosynthesis of fatty acids), storage of the lipids in the form of triglycerides, and lipolysis (hydrolysis of the triglycerides).

It turns out that, for various reasons (reaction with toxic compounds, disequilibrium between proteinic and lipidic anabolism, constraint on the free circulation of interstitial fluids, disequilibria of hormonal secretions), subcutaneous connective tissue can undergo an abnormal transformation, allowing itself to be progressively overcome by sclerosis. This syndrome, generally known as cellulite, is thus reflected in a morphological change in the skin and subcutaneous tissues.

Its terrain is almost exclusively female and its topography is localized on the pelvis, the lower limbs and, more incidentally, the abdomen.

The origin of the cellulitic tissue lesion is in the dermis and the hypodermis, the final appearance merely being the reflection of the structural changes in the deep layers of the skin.

Normally, the hypodermis or subcutaneous tissue forms a celluloadipose cushion in which connectivoelastic partitions separate the adipose lobules (rounded masses formed of adipocytes).

It is accepted that the number of adipocytes is fixed very early during growth and that the increase in adipose mass takes place primarily by hypertrophy (increase in the volume of the adipocytes).

The constitution of the celluloadipose tissue is due to two simultaneous anomalies: the accumulation of fat in the adipocytes and water retention by the ground substance.

Indeed, adipose tissue constitutes a considerable energy reserve stored in the form of intracellular triglycerides. These triglycerides can be hydrolysed to redistribute the fatty acids to the tissues. Lipolysis, adapted to the energy requirements, is constantly in equilibrium with lipogenesis.

The hydrolysis of triglycerides, carried out by the adipose tissue, gives it the role of being the main supplier of energy. It is due to the action of a hormone-sensitive enzymatic system which includes triglyceridelipase. This enzyme is activated by a cascade of reactions in which cyclic AMP (adenosine monophosphate) plays a central role.

Maintenance of the adipose mass depends on the correct functioning of all the systems of lipolysis regulation.

Lipolysis is regulated by many factors:

insulin, which blocks lipolysis and stimulates lipogenesis, glucagon, which brings about lipolysis within a few seconds, catecholamines (adrenaline and noradrenaline), which bring about a rapid and intense hydrolysis of triglycerides, other factors: thyroid hormones, glucocorticoids, growth hormone, etc.

Adipocytes have at their surface $\alpha$- and $\beta$-adrenergic receptors which play a major role in this regulation.

The binding of an agonist to the $\beta$-adrenergic receptor brings about the synthesis of cAMP, which is transmission of the signal. The increase in the intracellular concentration of cAMP indirectly activates the lipases and triggers lipolysis.

Two inhibitory mechanisms are involved in this chain of reactions:

the binding of an agonist to the $\alpha 2$-adrenergic receptor inhibits the transmission of the signal caused by a $\beta$-agonist, phosphodiesterase degrades the cAMP into 5'-AMP, which lowers the intracellular concentration of cAMP and limits lipolysis.

Thus, lipolysis can be stimulated by inhibiting phosphodiesterase (for example with caffeine or theophylline) or by activating the $\beta$-adrenoreceptors (for example with adrenaline). In the latter case, the stimulation will be potentiated if the $\beta 2$-adrenoreceptors are blocked (for example, the adrenaline+phentolamine combination).

Lipolysis can be demonstrated in vitro, in isolated human adipocyte models. The lipolysis can be monitored by assaying the release of fatty acids by the adipocytes.

The invention thus relates more particularly to a slimming composition which can be applied via the external topical route in order to stimulate the natural lipolytic activity which takes place physiologically in the body, or which is induced in vitro by the action of other molecules with demonstrated lipolytic activity.

The invention proposes to achieve these results by exploiting certain properties of *Chrysanthellum indicum*.

*Chrysanthellum indicum*, also known as *Chrysanthellum americanum* or *Chrysanthellum procumbens*, which is registered on the Pharmacopoeia list of medicinal plants in particular for its liver-protective, liver-stimulatory, antilithiasic, anti-oedematous and anti-inflammatory actions, contains phenylpropenoic acids, flavonoids and saponosides. It conjugates saponosides and flavonoids in a manner which is unusual in the plant world, and is exceptionally rich in flavonoids since it combines a flavone, an aurone, a chalcone and two flavonones, this combination also being highly uncommon in the plant kingdom.

This entirely surprising combination is the reason for the many virtues of *Chrysanthellum indicum,* which is a remedy used for the treatment of various complaints, of digestive, circulatory, etc. origin, such as:

hepatitis, colopathy, ictero-haemorrhagic syndromes, biliary and urinary lithiasis, cardiovascular and circulatory pathologies, etc.

In particular, *Chrysanthellum indicum* is recommended in the case of biliary insufficiency, post-hepatitis symtoms, alcoholic intoxication, salivary, renal or biliary lithiasis, enterocolitic disorders, vascular complaints and disruptions in lipid metabolism.

The studies reported show that treatments based on chrysanthellum are carried out orally (herbal infusion, plant extracts in syrup form, gelatin capsule form, etc.) or intraperitoneally, but never topically.

The only document reported which looks at the value of *Chrysanthellum indicum* in fields other than the strictly medical field is patent No. FR 2,618,071, which proposes cosmetic and dermatological compositions containing between 1% and 10% by weight of dry extract of chrysanthellum for applications such as shampoos and hair lotions, dermal emulsions, body milks and lipsticks, or even cosmetic compositions in the form of aerosols.

Besides the fact that that document does not relate to a cosmetic slimming composition, the recommended working concentrations lead to products that are entirely inappropriate for and even incompatible with normal cosmetic use, since, at these concentrations, emulsions for topical use have, in particular:

a dark brown colour which leads to the skin to be treated and the fingers used to apply the product being dyed an intense mustard-yellow. The strong intensity of this dyeing fades on rinsing but leaves a deep yellow colour after washing.

poor stability over time: a concentration of water in the bottom of the container and considerable release of oil at the surface are observed after 24 hours.

a strong odour of plant extract.

It turns out that even if it were theoretically possible to formulate a sufficiently stable product with such concentrations of chrysanthellum dry extracts, the coloration of this product would remain a major problem:

excessively intense colour, entirely at variance with what can generally be accepted by a user of cosmetic products.

product acting essentially as a dye: the skin and the nails are unavoidably dyed a more or less intense yellow. Similarly, tissue which comes into contact with this product is indelibly dyed a more or less intense yellow which turns orange after washing with the usual detergents.

The aim of the invention is thus, more particularly, to develop a slimming composition which can be administered topically, which uses the active principles of *Chrysanthellum indicum* as slimming composition material and which solves the problems both of coloration and of odour, mentioned above.

The invention achieves this result by means of a composition comprising an extract of *Chrysanthellum indicum* at low concentration containing from 0.0001% to 0.1%, i.e. from 1 μg/ml to 1000 μg/ml of dry extract equivalents of *Chrysanthellum indicum.*

Moreover, there is nothing in the literature to indicate that *Chrysanthellum indicum* could have lipolytic activity: this activity, which was discovered fortuitously, appears in an entirely appreciable manner during the implementation of studies and experiments which are described hereinbelow:

Study No. 1

The first study relates to a dry extract of *Chrysanthellum indicum.*

This extract and reference products (adrenaline, theophylline, caffeine) were placed in contact with an appropriate number of cells (human adipocytes) for 2 hours at 37° C. Control incubations (cells without product) or controls (products without the cells) were carried out in parallel.

The effects were then evaluated by measuring the cell lysis (which reflects the cytotoxicity) and measuring the lipolytic activity.

This first study showed that, under the experimental conditions adopted, the dry extract of *Chrysanthellum indicum* was not cytotoxic on human adipocytes in suspension and had no lipolytic properties.

Study No. 2

This study relates to a dry extract of *Chrysanthellum indicum* and an extract in aqueous-glycolic solution.

This study evaluates the potentiating effect of extracts of *Chrysanthellum indicum* on the lipolytic activity of caffeine and adrenaline in isolated human adipocytes.

The potentiating effect of the test products was studied in the same model, i.e. a suspension of isolated human adipocytes (the target cells of the "slimming" products). The potentiation of the lipolytic effect of caffeine and adrenaline was assessed by measuring the hydrolysis of the triglycerides. The triglyceride hydrolysis was monitored by assaying the unesterified fatty acids released into the adipocyte incubation medium.

Adrenaline stimulates lipolysis by binding to membrane receptors (β-adrenergic receptors). Caffeine promotes triglyceride hydrolysis by increasing the intracellular concentration of cyclic AMP by inhibition of phosphodiesterase.

During the tests, combinations (test extract+caffeine or adrenaline) and reference products (adrenaline and caffeine) were placed in contact with an appropriate number of cells for 2 hours at 37° C. Incubations "cells-without-product controls" or "products-without-cell controls" were carried out in parallel.

The effects were evaluated by assaying the unesterified fatty acids released into the incubation medium (expressed in nanomoles of fatty acids released into the adipocyte medium).

The groups of data (control groups and treated groups) were compared by a factor variance analysis (Anova 1), followed by a Dunnett test. The effects of the combinations "test extracts+caffeine or adrenaline" were compared with those observed in the presence of caffeine or adrenaline alone.

These tests showed that the dry extract of *Chrysanthellum indicum* at 0.02% (w/v) significantly potentiates the effect of $10^{-6}$ M adrenaline by a factor of 1.8. On the other hand, at this concentration, it does not potentiate the activity of $10^{-4}$ M caffeine.

Similarly, the extract of *Chrysanthellum indicum* in glycolic solution tested at 0.1% (w/v) significantly potentiates the effect of $10^{-6}$ M adrenaline by a factor of 1.6. At this concentration, it does not potentiate the lipolytic activity of $10^{-4}$ M caffeine.

The reason for this potentiation effect on the lipolytic activity of $10^{-6}$ M adrenaline may be linked to a mechanism of action of α2-antagonist type: in the adipocytes, the activation of the β-adrenergic receptors activates lipolysis. This action is inhibited by the stimulation of the α2-adrenergic receptors. A molecule which has an activity of α2-antagonist type allows this "brake" to be released and allows the lipolytic activity of the products of β-adrenergic type to be increased. A complementary "binding" study makes it possible to determine the binding capacities of the *Chrysanthellum indicum* dry extracts or extracts in glycolic solution to the α2-adrenergic receptors and to support the suggested hypothesis.

Complementary tests showed that this potentiation effect on the lipolytic activity of adrenaline was exhibited for concentrations of *Chrysanthellum indicum* (dry extracts or extracts in glycolic solution) ranging from 0.00025% to 0.075% of dry extract equivalents.

It thus turns out that, on account of its potentiating action on the lipolytic activity of adrenaline (a fundamental molecule in the process of in vivo lipolysis regulation), irrespective of the form it is in, the extract of *Chrysanthellum indicum* is an active agent of choice in the context of an investigation of slimming.

It facilitates the hydrolysis of the excess triglycerides stored in the adipocytes (fatty tissue cells) and the release of the fatty acids resulting from this hydrolysis.

Its use is thus particularly recommended for the formulation of any bodycare product intended for slimming: emulsions (water/oil or oil/water creams or milks), aqueous or oily gels, aqueous or aqueous-alcoholic lotions, multiple emulsions, microemulsions, emulsions with liquid crystals, or controlled-release or modulated-release vectorized systems.

As has been seen, the processes for storing and hydrolysing the fats in adipose tissue are complex processes involving a large number of molecules and mechanisms of action.

Thus, a bodycare product intended for slimming, preventive and/or curative treatment of cellulite and of the various consequences of a fatty overload of the skin, must, in order to have maximum efficacy, preferably contain complementary active principles capable of promoting or potentiating various mechanisms of action.

Thus, the extracts of *Chrysanthellum indicum* may be combined with various active principles such as, for example:

phosphodiesterase inhibitors (theophylline, caffeine, guaranine, etc.),

β-agonists (β-adrenergic receptor stimulants), etc., molecules which facilitate the transportation of fatty acids across cell membranes (L-carnitine, etc.), connective tissue "regenerating agents" (silanols, plant extracts such as *Centella asiatica,* etc.), decongestants or infiltration inhibitors (extracts of algae, of pineapple, of mouse-ear hawkweed, etc.), draining agents (extracts of ivy, etc.), anti-radical substances and antioxidants (extracts of *Ginkgo biloba,* of green tea, etc.), blood microcirculation stimulants (tri-oxy-esters of glycerol, plant extracts such as common horse chestnut, Scotch pine, etc.), etc.

Composition formulation examples will be described below by way of non-limiting examples.

| Example I: Slimming gel I | |
|---|---|
| Ethoxylated sorbitan stearate | from 0.5 to 1% |
| Plant oils and/or mineral oils and/or emollient esters | from 10 to 15% |
| Antimicrobial preserving agents | from 0.5 to 1% |
| Demineralized water | qs 100% |
| Moisturizer | from 1 to 5% |
| Acrylic gelling agent | from 0.5 to 1% |
| Triethanolamine or sodium hydroxide | from 0.1 to 1% |
| Fragrance | from 0.1 to 1% |
| Aqueous-glycolic solution of extract of Chrysanthellum indicum | from 0.5 to 2% |

| Example II: Slimming cream | |
|---|---|
| Sorbitan stearate | from 1 to 2% |
| PEG-100 stearate and glyceryl stearate | from 2 to 4% |
| Mineral oils and/or plant oils and/or emollient esters | from 10 to 15% |
| Demineralized water | qs 100% |
| Moisturizer | from 1 to 5% |
| Acrylic gelling agent | from 0.1 to 1% |
| Triethanolamine or sodium hydroxide | from 0.1 to 1% |
| Antimicrobial preserving agents | from 0.1 to 1% |
| Gelling agent (for example such as Sepigel, sold by the company SEPPIC) | from 0.2 to 1% |
| Fragrance | from 0.1 to 1% |
| Aqueous-glycolic solution of extract of Chrysanthellum indicum | from 0.1 to 0.5% |

| Example III: Slimming gel II | |
|---|---|
| Demineralized water | qs 100% |
| Glycerol | from 1 to 5% |
| Acrylic gelling agent | from 0.1 to 1% |
| Triethanolamine or sodium hydroxide | from 0.1 to 1% |
| Antimicrobial preserving agents | from 0.5 to 1% |
| Plant oils and/or mineral oils | from 1 to 5% |
| Fragrance | from 0.1 to 1% |
| Aqueous-glycolic solution of extract of Chrysanthellum indicum | from 0.5 to 2.5% |

| Example IV: Massage cream | |
|---|---|
| Sorbitan stearate | from 1 to 2% |
| Glyceryl stearate | from 3 to 7% |
| Stearic acid | from 2 to 5% |
| Mineral oils and/or plant oils and/or emollient esters | from 15 to 20% |
| Antioxidant | from 0.02 to 0.05% |
| Demineralized water | qs 100% |
| Moisturizer | from 2 to 6% |
| Triethanolamine or sodium hydroxide | from 0.5 to 1% |
| Gelling agent (for example such as Sepigel, sold by the company SEPPIC) | from 0.5 to 3% |
| Antimicrobial preserving agents | from 0.5 to 1% |
| Fragrance | from 0.1 to 1% |
| Aqueous-glycolic solution of extract of Chrysanthellum indicum | from 0.1 to 1% |

As mentioned above, in the composition according to the invention, the extract of *Chrysanthellum indicum* may be a dry extract or an extract in glycolic solution. However, the invention is not limited to this characteristic, since the extract may be fluid, may be encapsulated in an aqueous or oily continuous phase or may be in solution in a water/glycerol mixture.

Similarly, the composition may be in various forms: simple emulsion—oil/water or water/oil cream or milk—multiple emulsion, microemulsion or emulsion containing liquid crystals—aqueous or oily gels—aqueous or aqueous-alcoholic lotion—controlled-release or modulated-release vectorized system.

In the examples described above, the dry extract of *Chrysanthellum indicum* is obtained conventionally by grinding the fresh or dry plant until a powder is obtained. This powder is macerated in water optionally mixed with ethanol or methanol. From this macerate, an extract is obtained by lixiviation and, once washed, this extract is concentrated and then evaporated to dryness. A water-soluble powder is obtained, which can be used in solution in water or even as an aqueous-glycolic solution (butylene glycol or propylene glycol), or alternatively as a solution in a water/glycerol mixture.

What is claimed is:

1. Cosmetic slimming composition which can be administered topically for the preventive and/or curative treatment of cellulite, said cosmetic slimming composition comprising an extract of *Chrysanthellum indicum* at low concentration containing from 0.0001% to 0.1% of dry extract equivalents of *Chrysanthellum indicum*.

2. Composition according to claim 1, wherein the above-mentioned extract is a dry extract of *Chrysanthellum indicum*.

3. Composition according to claim 1, wherein the above-mentioned extract is a fluid extract of *Chrysanthellum indicum*.

4. Composition according to claim 2, wherein the above-mentioned dry extract is in solution.

5. Composition according to claim 4, wherein the above-mentioned dry extract is in glycolic solution.

6. Composition according to claim 4, wherein the above-mentioned dry extract is in solution in a water/glycerol mixture.

7. Composition according to claim 1, comprising an extract of *Chrysanthellum indicum* encapsulated in an aqueous or oily continuous phase.

8. Composition according to claim 1, wherein said composition consists of simple emulsions.

9. Composition according to claim 8, wherein said composition is a water/oil or oil/water cream or milk.

10. Composition according to claim 8, wherein said composition is a multiple emulsion, a microemulsion or an emulsion containing liquid crystals.

11. Composition according to claim 1, wherein said composition is aqueous gels.

12. Composition according to claim 1, wherein said composition is an aqueous lotion.

13. Composition according to claim 1, wherein said composition is a controlled-release vectorized system.

14. Composition according to claim 1, comprising β-agonists which act as β-adrenergic receptor stimulants.

15. Composition according to claim 1, comprising molecules which facilitate the transportation of fatty acids across cell membranes.

16. Composition according to claim 1, comprising connective tissue regenerating agents.

17. Composition according to claim 1, comprising decongestants.

18. Composition according to claim 1, comprising draining agents.

19. Composition according to claim 1, comprising anti-radical substances and antioxidants.

20. Composition according to claim 1, comprising blood microcirculation stimulants.

21. Composition according to claim 1, wherein said composition is multiple emulsions.

22. Composition according to claim 1, wherein said composition is oily gels.

23. Composition according to claim 1, wherein said composition is an aqueous-alcoholic lotion.

24. Composition according to claim 1, wherein said composition is a modulated-release system.

25. Composition according to claim 1 comprising L-carnitine.

26. Composition according to claim 1 comprising silanols.

27. Composition according to claim 1 comprising plant extracts.

28. Composition according to claim 1, comprising *Centella asiatica*.

29. Composition according to claim 1, comprising infiltration inhibitors.

30. Composition according to claim 1, comprising extracts of algae.

31. Composition according to claim 1, comprising extracts of pineapple.

32. Composition according to claim 1, comprising extract of mouse-ear hawkweed.

33. Composition according to claim 1, comprising extract of ivy.

34. Composition according to claim 1, comprising extracts of *Ginkgo biloba*.

35. Composition according to claim 1, comprising extracts of green tea.

36. Composition according to claim 1, comprising tiroxy-esters of glycerol.

37. Composition according to claim 1, comprising plant extracts of common horse chestnut.

38. Composition according to claim 1, comprising plant extracts of scotch pine.

* * * * *